US008910625B2

(12) United States Patent
Mullinger et al.

(10) Patent No.: US 8,910,625 B2
(45) Date of Patent: Dec. 16, 2014

(54) INHALATION DEVICE FOR USE IN AEROSOL THERAPY

(71) Applicant: Vectura GmbH, Gemunden (DE)

(72) Inventors: Bernhard Mullinger, Munich (DE); Tobias Kolb, Neuried (DE); Martin Huber, Fürstenfeldbruck (DE); Tobias Hoffmann, Gilching (DE)

(73) Assignee: Vectura GmbH, Gemunden (DE)

( * ) Notice: Subject to any disclaimer, the term of this patent is extended or adjusted under 35 U.S.C. 154(b) by 0 days.

(21) Appl. No.: 14/063,115

(22) Filed: Oct. 25, 2013

(65) Prior Publication Data

US 2014/0116426 A1 May 1, 2014

(30) Foreign Application Priority Data

Oct. 26, 2012 (EP) .................................... 12190139

(51) Int. Cl.
*A61M 11/00* (2006.01)
*B05B 17/06* (2006.01)
*A61M 15/00* (2006.01)
*A61M 16/00* (2006.01)

(52) U.S. Cl.
CPC ......... *A61M 15/009* (2013.01); *A61M 15/0021* (2013.01); *A61M 11/005* (2013.01); *A61M 2205/6045* (2013.01); *A61M 2016/0027* (2013.01); *A61M 2205/584* (2013.01); *A61M 2205/3584* (2013.01); *A61M 15/002* (2013.01); *A61M 15/0085* (2013.01); *A61M 2016/0033* (2013.01); *A61M 2016/003* (2013.01); *A61M 15/0091* (2013.01); *A61M 2205/8206* (2013.01); *A61M 2205/52* (2013.01); *A61M 2205/276* (2013.01); *A61M 15/00* (2013.01); *A61M 2205/583* (2013.01)
USPC ................................ 128/200.16; 128/200.14

(58) Field of Classification Search
USPC ............ 128/200.14, 200.16, 200.22, 200.23, 128/202.27, 203.15
See application file for complete search history.

(56) References Cited

U.S. PATENT DOCUMENTS

| 7,721,734 B2 * | 5/2010 | Rustad et al. ............ 128/203.12 |
| 2002/0157664 A1 * | 10/2002 | Fugelsang et al. ....... 128/200.22 |
| 2008/0163869 A1 | 7/2008 | Nobutani |
| 2009/0095292 A1 | 4/2009 | Hamano et al. |
| 2010/0044460 A1 | 2/2010 | Kobayashi et al. |
| 2010/0154793 A1 | 6/2010 | Hamano et al. |
| 2010/0180890 A1 | 7/2010 | Sauzade |
| 2010/0326436 A1 | 12/2010 | Kaneko |
| 2013/0104887 A1 | 5/2013 | Smutney et al. |

OTHER PUBLICATIONS

Search report mailed Mar. 15, 2013 from corresponding EP application No. 12190139.1.

* cited by examiner

*Primary Examiner* — Kristen Matter
(74) *Attorney, Agent, or Firm* — Kagan Binder, PLLC

(57) ABSTRACT

An inhalation device having a base unit, a mouthpiece, and an aerosol head is provided. The base unit has an air inlet, an air outlet opening, a groove for receiving the mouthpiece, and key lock member(s). The mouthpiece has two segments: a first segment which is insertable into the groove of the base unit and has an air inlet opening and a lateral opening for receiving an aerosol generator and a second segment with an aerosol outlet. The aerosol head has an aerosol generator, a liquid reservoir, and key lock member(s) complementary to those of the base unit. The base unit, mouthpiece and aerosol head are connectible with one another such that when engaging the members of the key lock with the complementary members, the aerosol generator is inserted into the lateral opening of the mouthpiece.

15 Claims, 8 Drawing Sheets

INHALATION DEVICE FOR USE IN AEROSOL THERAPY

CROSS-REFERENCE TO RELATED APPLICATION

This application claims priority to EP application no. 12 19 0139.1 filed Oct. 26, 2012.

BACKGROUND

Inhalation devices which allow a patient to inhale an aerosol are required for numerous medical applications, such as the inhalative treatment of asthma, cystic fibrosis (CF), and a number of other respiratory diseases. An aerosol is a dispersion of small solid particles or liquid droplets in a continuous gas phase. Typically, aerosols of fine droplets of a liquid formulation of a bioactive agent or drug are required in medical inhalation treatments; ideally reaching even the smallest branches of the peripheral lungs, such as bronchioles and alveoli.

In order to achieve the desired homogeneous droplet distribution in the gas phase, the liquid formulation in the inhalation device is atomised by nebulisers, such as ultrasonic nebulizers, jet nebulizers or vibrating mesh nebulizers.

The individual components of currently available vibrating mesh nebulizers, such as, for example, the liquid reservoir, the aerosol generator comprising the vibrating mesh, the mixing chamber and the mouthpiece, are typically assembled so that the nebulizer membrane is either arranged approximately vertical or horizontal.

With vertically arranged nebulizer membranes, the generated aerosol is introduced horizontally into the air flow channel, and the aerosol generator can be positioned at an angle to the direction of the air flow, without thereby changing the vertical arrangement of the membrane. Depending on the selected angle, it is even possible to introduce the aerosol roughly in parallel with the air flow. This approach is, for example, chosen by PARI (e.g. WO 2009/135871 A1) and may, in addition, be complemented with an annular air stream surrounding the aerosol generator so that the nascent aerosol is engulfed in air to avoid particle collision with the inner walls of the mouthpiece. Thereby this "air jacket" as well as the option to orient the aerosol generator at an angle to the direction of the air flow eliminates the need for spacious mixing chambers. However, since the liquid has to be supplied to a vertically positioned nebulizer membrane, even minor handling deviations such as tilting the device during inhalation lead to distinct variations in liquid supply and consequently the volume inhaled as an aerosol. Also, the residual volume remaining in the reservoir at the end of the inhalation treatment is typically higher than for inhalation devices with a horizontally arranged nebulizer membrane. In addition, errors during assembly of the inhalation device as well as the vertical arrangement of the nebulizer membrane commonly create problems with providing airtight, leakproof connections between the aerosol generator and the air flow channel.

Horizontally arranged nebulizer membranes allow for an easier, gravity-driven and thus less variable supply of the liquid from a reservoir above said membrane. However, the generated aerosol is now introduced perpendicular into the air flow channel, so that typically mixing chambers are required in order to avoid particle collision with each other and/or the device's inner walls and to homogeneously mix the aerosolized particles with the air flow before inhalation by the user. Typically, these mixing chambers are rather spacious and hence increase the dimensions of the inhalation devices unfavourably. Furthermore, owing to longer residence times of the aerosol in the mixing chamber and turbulences within said mixing chamber sedimentation and impaction of the aerosolized particles occur, thereby increasing wastage of the aerosolized formulation as well as decreasing dose reproducibility. Also, the vertically stacked arrangement of liquid reservoir, aerosol generator (with horizontal membrane) and mixing chamber, leads to devices which are rather high compared to their width. This could lead to handling problems because devices may easily fall on their side, especially upon filling of the reservoir or in filled state.

Further problems may arise during the assembly of the nebulizer, when patients put the individual components of the inhalation device together incorrectly, for example, after cleaning and/or disinfecting them as required. This could lead to irreproducible dosing of active agents due to leakage of the liquid, malfunctions such as pressure losses, reduced therapeutic efficacy or even permanent damages to the device. Especially sick and/or elderly users may become discouraged by complicated dissembling-and assembling routines and either stop to comply with their therapy or stop to dissemble and clean their device regularly. This provokes a worsening of symptoms and/or increases the risk for infections of the respiratory tract from contaminated devices.

WO 2008/050542 A1 discloses a portable inhalation device comprising a main body, a detachable mouthpiece, an inkjet system medicine cartridge and a slide-on cover. The main body comprises an air flow path and two fitting portions where the medicine cartridge and the mouthpiece can be inserted in such a way that they are in fluid communication with the air flow path. The medicine cartridge comprises a reservoir (as an integral or detachable part), electrical connectors and an ejection head, preferably equipped with a heater, from which medicine is ejected by thermal energy using the principle of inkjet systems. As an alternative to such electro-thermal ejection means electro-mechanical ejection means are suggested, such as by piezo-electric devices. After its insertion into the fitting portion, the medicine cartridge is fixed to the main body by the slide-on cover.

WO 2008/050542 A1 does not describe key lock members or similar features of the medicine cartridge or of the main body which would ensure easy and correct assembly, i.e. the complete insertion of the medicine cartridge in the right orientation, and securely lock the components together. Furthermore, the first segment of the mouthpiece in WO 2008/050542 A1 (i.e. the communicating portion which is inserted into the main body) does not comprise a lateral opening for receiving the ejection head of the medicine cartridge. Therefore the aerosol is emitted directly into the air flow path of the main body before entering the first segment of the mouthpiece. In this manner, some aerosol will inevitably be deposited within the main body. In consequence, this does not only lead to an increased loss of aerosol, but is also associated with the disadvantage that the user would have to clean not only the detachable mouthpiece but also the air flow path in the opened main body which houses the water-sensitive electronic controls for the ejection head and further electrical components.

WO 2006/083014 A1 describes a similar portable inhaling apparatus comprising a main body provided with a fitting section for removably fitting thereto a disposable liquid agent ejection cartridge. The ejection cartridge comprises a storage tank for a liquid agent, an ejection head with ejection means, an integral mouthpiece (called suction port) and a flow path projecting from the cartridge. The ejection head may be an ink-jet head comprising a heater or a piezoelectric element or one having a mesh structure with a large number of pores. The mouthpiece is an integral part of the ejection cartridge, as favoured by the authors, and therefore the mouthpiece must be discarded along with the cartridge every time the storage tank is empty, as the storage tank cannot be effectively cleaned and/or refilled by a user. Moreover, the document is silent about key locks or any other features of this type which would ensure easy, correct and complete assembly of the device. Further, the device does not exhibit a mouthpiece having a lateral opening for receiving an aerosol generator capable of emitting an aerosol into the flow path of the mouthpiece.

It is thus the aim of the current invention to provide an improved inhalation device comprising a low number of components which ensure the fast and correct assembly and filling of the device as well as to improve its air tightness and reduce pressure losses and leakages by reducing the number of leak-prone connections. Another aim of the current invention is to allow for easier, safer cleaning operations. It is further the aim of the current invention to facilitate effective customization by providing inhalation devices comprising aerosol generators which are tailor-made for specific therapies, wherein said aerosol generators can be assembled only with its intended counter-components.

SUMMARY OF THE INVENTION

The objectives of the invention are met by the inhalation device according to the claims. Advantageous embodiments are also provided in the dependent claims.

In particular, an inhalation device is provided which comprises a base unit, a mouthpiece and an aerosol head which are connectable with one another. The base unit comprises one or more air inlet opening(s), an air outlet opening, a groove for receiving the mouthpiece, and one or more key lock member(s) which may e.g. be male or female. The mouthpiece comprises a first segment and a second segment, the second segment being downstream of the first segment. The first segment comprises an air inlet opening which may be attachable to the air outlet opening of the base unit, and a lateral opening for receiving an aerosol generator, and the second segment comprises an aerosol outlet opening. The aerosol head includes an aerosol generator, a reservoir for a liquid and one or more key lock member(s) which may be male or female, and which are complementary to the key lock member(s) of the base unit. The aerosol generator is positioned in the aerosol head in such a way that when engaging the male or female key lock member(s) of the aerosol head with the complementary key lock member(s) of the base unit, the aerosol generator is at least partially inserted into the lateral opening of the first segment of the mouthpiece.

The groove in the base unit and the mouthpiece inserted therein may have a horizontal orientation. Moreover, the groove may extend from the air outlet opening of the base unit to the front side of the base unit. It may not be the complete mouthpiece which is accommodated in the groove, but only a portion thereof, e.g. the proximal segment or first segment.

The lateral opening of the mouthpiece which receives the aerosol generator may be positioned on the top side of the first segment of the mouthpiece, so that the aerosol generator, which may be of the vibrating mesh type, is inserted vertically into the mouthpiece.

The first segment of the mouthpiece may comprise a protrusion.

The base unit may comprise an indentation for receiving the protrusion.

The protrusion as well as the indentation may be asymmetric.

The base unit and the aerosol head may each comprise two key lock members.

The key lock members may be positioned to form a key lock on the left side and another key lock on the right side of the inhalation device.

The key locks may be disengaged by squeezing the aerosol head at the position of the key lock members.

The aerosol generator may have an upstream end positioned at the top of the aerosol generator and a downstream end positioned at the bottom of the aerosol generator.

The mesh of the aerosol generator may be located at or near the downstream end of the aerosol generator.

The air outlet opening of the base unit may exhibit a sealing member.

Alternatively, the lateral opening of the mouthpiece for receiving the aerosol generator may exhibit a sealing member.

As a further alternative, the air outlet opening of the base unit and the lateral opening of the mouthpiece for receiving the aerosol generator may exhibit a sealing member.

The air outlet opening may, for example, be circular or elliptical and may, for example, be positioned in a central region of the base unit. Optionally, the base unit may exhibit more than one air outlet opening.

The base unit and the aerosol head may comprise electrical connectors positioned in such a way that when engaging the base unit's member(s) of the key lock with the aerosol head's complementary member(s) the electrical connectors of the base unit are brought in contact with the electrical connections of the aerosol head.

The base unit may comprise one or more sensor(s) for sensing air pressure or air flow rate within the unit.

The base unit may comprise valve for opening or closing the air flow within the unit.

The base unit may comprise an electronic control unit for controlling the aerosol generator.

The base unit may comprise an electronic control unit for controlling the valve.

Alternatively, the base unit may comprise one or more sensor(s) for sensing air pressure or air flow rate within the unit, and a valve for opening or closing the air flow within the unit.

Alternatively, the base unit may comprise one or more sensor(s) for sensing air pressure or air flow rate within the unit, and an electronic control unit for controlling the aerosol generator and/or the valve.

Alternatively, the base unit may comprise a valve for opening or closing the air flow within the unit, and an electronic control unit for controlling the aerosol generator and/or the valve.

Further alternatively, the base unit may comprise (a) one or more sensor(s) for sensing air pressure or air flow rate within the unit, and a valve for opening or closing the air flow within the unit, and an electronic control unit for controlling the aerosol generator and/or the valve.

The inhalation device may further comprise a feedback system.

The feedback system may comprise one or more sensor(s) for sensing air pressure or air flow rate capable of generating a sensor signal in response to an actual value of flow rate and/or inhaled volume during the inhalation manoeuvre. The feedback system may also comprise an electronic memory capable of storing one or more target values and/or target ranges for flow rate and/or inhaled volume. Furthermore, the feedback system may comprise one or more feedback indicator(s) capable of emitting an output signal. The feedback system may also comprise a controller capable of receiving the sensor signal(s) generated by the sensor(s), reading the electronic memory, and controlling the one or more feedback indicator(s).

The feedback system may be is configured to indicate to a user during an inhalation manoeuvre by means of the output signal(s) whether the actual value of the flow rate and/or inhaled volume is within a target range.

The one or more air inlet opening of the base unit may be positioned at the rear side of the device or base unit.

The one or more air inlet opening(s) of the base unit may be connected to a tube through which an air flow is received.

The tube optionally exhibits a first lumen for an air flow and a second lumen holding an electrical wire.

The inhalation device may be configured as a mobile, stand-alone device with the inspiratory flow being generated by the user.

The inhalation device may further comprise a flow restrictor configured to restrict, control and/or regulate the inspiratory air flow of the patient, or to assist the patient to adopt a useful inspiratory flow rate. The flow restrictor may be configured to enable the patient or user to achieve a preset specific target value, for example 15 L/min, or target range, such as from 12 to 18 L/min.

According to another aspect, the invention provides the use of the inhalation device according to any of the above aspects and features for inhalation therapy.

The invention allows easy assembly and disassembly of the inhalation device by the user as well as easier, safer cleaning routines and provides for increased product safety in that it ensures that the device is assembled in a correct manner. Moreover, the low number of components to be assembled requires very few airtight connections so that the risk of leakage or pressure loss is minimised.

Further advantageous embodiments, features, beneficial effects and uses of the device are described below in more detail.

Definitions

The following expressions as used herein should normally be interpreted as outlined in this section, unless the description provides a different meaning in a specific context.

"Lateral", or "laterally", means away from the middle, centre, or centre axis of a device or device component.

"Front", such as in "front side" or "front face", as well as all similar terms designating a position, orientation or direction, such as left, right, rear, back, top, bottom, up, down and the like, should be understood with reference to the orientation of the inhalation device or its components under normal operational conditions, and typically from the perspective of the user. For the avoidance of any misunderstandings, it is clear that a user may also hold the device in such a way that there is some deviation from a normal operational orientation. For example, while the device is designed to be held in an approximately horizontal orientation with respect to the axis along which the air flow within the device occurs, the user may also hold the device at an angle of up to 45° deviating from the horizontal orientation, without negative impact on the device function. Similarly, a user may, to some degree, rotate the device around said axis, again without any substantial deterioration of device performance.

"Key lock" is understood as a locking mechanism for connecting parts or components mechanically in a detachable manner using at least one pair of members with complementary shape such as to engage with each other non-permanently. Click mechanisms, or snap-fit mechanisms, are examples of key locks.

"Key lock member" is a member (e.g. a male member) having a particular shape adapted for non-permanent mechanical engagement with a complementary (e.g. a female member) member such as to connect two devices in a detachable manner.

"Flow," such as in "air flow" or "inspiratory flow" refers to the rate of flow.

"Comprise" or "comprising" with reference to any feature means that the respective feature must be present, but without excluding the presence of other features.

"A" or "an" does not exclude a plurality.

"Essentially", "about", "approximately" and the like in connection with an attribute or value include the exact attribute or the precise value, as well as any attribute or value typically considered to fall within a normal range or variability accepted in the technical field concerned.

Any reference signs in the claims should not be construed as a limitation to the embodiments represented in any of the drawings.

A single unit may fulfil the functions of several features recited in the claims.

LIST OF NUMERICAL REFERENCES USED IN THE FIGURES

Figure 1:
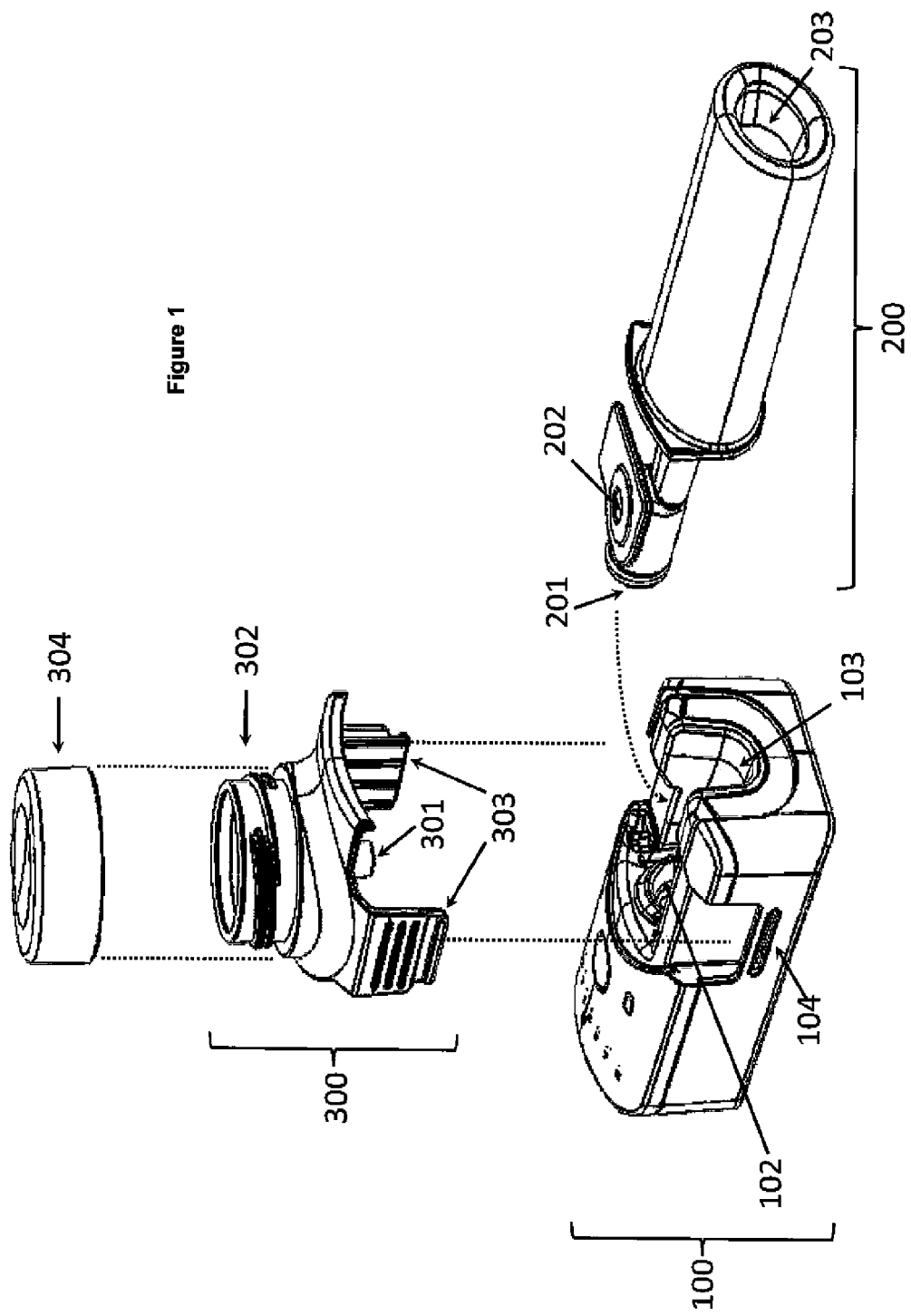
FIG. 1 shows an exploded view of a particular inhalation device according to the invention according to one embodiment of the invention in the dissembled state.

100 Base unit
101 Air inlet opening
102 Air outlet opening
103 Groove
104 Key lock member
105 Sealing member
106 Indentation
107 Indentation
108 Electrical connector
109 Electrical connector
110 Air channel
111 Power switch
112 on/off indicator
113 Battery indicator
114 Connectivity indicator
115 Inhalation time indicator
116 Flow restrictor
117 Feedback indicator
118 Valve
119 Sensor
200 Mouthpiece 200a First segment of mouthpiece
200b Second segment of mouthpiece
201 Air inlet opening
202 Lateral opening
203 Aerosol outlet opening
204 Protrusion
205 Sealing member
206 Step
207 Air channel
300 Aerosol head
301 Aerosol generator
302 Reservoir
303 Key lock member
304 Lid
305 Protrusion
306 Piezoelectric transducer body
306a Upstream end
306b Downstream end
306c Stress concentration zone
306d Deformation amplification zone
307 Cavity containing liquid to be nebulized
308 Piezoelectric member
309 Mesh

DETAILED DESCRIPTION OF THE INVENTION

The invention provides, inter alia, an inhalation device comprising a base unit, a mouthpiece, and an aerosol head. The base unit (100) comprises one or more air inlet opening(s) (101), an air outlet opening (102), a groove (103) for receiving the mouthpiece (200), and one or more key lock member(s) (104), e.g. male or female member(s). The mouthpiece (200) comprises a first segment (200a), comprising an air inlet opening (201) which may be attachable to the air outlet opening (102) of the base unit (100), and a lateral opening (202) for receiving an aerosol generator (301), the first segment (200a) being insertable into the groove (103) of the base unit (100), and a second segment (200b) downstream of the first segment (200a), comprising an aerosol outlet opening (203). The aerosol head (300) comprises an aerosol generator (301), a reservoir for a liquid (302), and one or more male or female key lock member(s) (303) complementary to the male or female key lock member(s) (104) of the base unit (100). The base unit (100), the mouthpiece (200) and the aerosol head (300) are connectable with one another.

The assembly of the base unit (100) with the mouthpiece (200) and aerosol head (300) is easily achieved, e.g. by inserting the first segment (200a) of the mouthpiece (200) into the groove (103) in the base unit (100), then placing the aerosol head (300) over said first segment (200a) of the mouthpiece (200) and engaging the key lock member(s) (303) of the aerosol head (300) with the complementary member(s) (104) of the base unit (100) by gentle pressure on both the aerosol head and the base unit. These few assembling steps will typically create airtight connections between the base unit's (100) air outlet opening (102) and the air inlet opening (201) of the mouthpiece's first segment (200a) as well as between the aerosol generator (301) and the lateral opening (202) in the mouthpiece's first segment (200a). Moreover, the aerosol generator (301) is positioned in the aerosol head (300) in such a way that when engaging the member(s) of the key lock with the complementary member(s), the aerosol generator (301) is at least partially inserted into the lateral opening (202) of the first segment (200a) of the mouthpiece (200).

The inhalation device according to this invention is designed to be useful for inhalation therapy. Specifically, it is for delivering nebulised aerosols to individuals in need thereof. Such devices are often referred to as nebulisers, which have in common that they convert a liquid into an aerosol, i.e. into a system having at least two phases, of which the continuous phase is gaseous and comprises a dispersed liquid phase in the form of small liquid droplets. Optionally, the liquid phase may itself represent a liquid solution, dispersion, suspension, or emulsion.

Aerosols for inhalation therapy often, but not always, comprise an active ingredient such as a drug substance useful in the prevention, management, treatment or alleviation of a disease, condition or symptom. The drug substance, often also referred to as drug, active compound, pharmaceutical, active pharmaceutical ingredient (API), or bioactive agent, may be dissolved, dispersed or suspended in a liquid—typically aqueous—carrier such as to form an aerosolisable, or nebulisable, drug formulation. Of course, the formulation may also comprise two or more active ingredients.

The inhalation device enables oral inhalation of the nebulised aerosol, i.e. inhalation via the mouth, which is typically the preferred route of administration of aerosols to the lungs. Preferably, the inhalation device is designed as a relatively small, hand-held device which may be used either as a mobile, stand-alone nebuliser or as a handset for an inhalation system comprising further hardware components such as a control unit capable of providing a controlled air flow to the inhalation device, such as to control the inspiratory flow rate and/or inhalation volume of the individual receiving the aerosol treatment. In contrast, with a mobile stand-alone device, the inspiratory flow is normally generated by the user.

In one embodiment, the shape of the device according to this invention is roughly cuboidal, optionally with rounded edges. Owing to the omission of a spacious mixing chamber (as will be described in further detail below), the dimensions of the device can be chosen in such a way that the height of the device, with the aerosol head (300) attached, is not greater, or only marginally greater than its width when looked at from the front, i.e. the side facing the user during inhalation. This prevents tilting or tipping of the device during filling of the reservoir (302) or when put down in the empty or filled state.

As mentioned, the inhalation device comprises three major components which are connectable with one another, i.e. a base unit (100), a mouthpiece (200) and an aerosol head (300). The base unit (100) may also be understood as the basis or socket of the device to which the other components are connected. According to the invention, the base unit (100) comprises one or more air inlet opening(s) (101) and an air outlet opening (102).

Through the outlet opening (102) of the base unit (100), air flows into the mouthpiece (200) via the air inlet opening (201) of its first segment (200a). The air outlet opening (102) may, for example, be circular or elliptical and may, for example, be positioned in a central region of the base unit (as e.g. shown in FIG. 1). It may further exhibit a sealing member (105), for example in form of a gasket, a sealing lip, gaiter, or any other type of seal, which serves to provide an airtight connection with the air inlet opening (201) of the mouthpiece (200). Optionally, the base unit (100) may exhibit more than one air outlet opening.

The one or more air inlet opening(s) (101) may, for example, be positioned at the rear side of the device or base unit (100), e.g. in order to avoid their potential obstruction by the user's hand during inhalation. As used herein, the rear—or rear side—means the side or face of the device or device component which is opposite to the front, or front side, which in turn is the side or face of the device or device component that faces the user during inhalation.

The air inlet opening(s) (101) and the air outlet opening (102) are typically connected within the base unit (100) such as to form an air channel (110) wherein, under operational conditions and during the inspiratory phase of the breathing manoeuvre of a user, air flows from the upstream end to the downstream end of the air channel (110), i.e. from the air inlet opening(s) (101) to the air outlet opening (102) of the base unit (100).

The base unit (100) further comprises a groove (103) (or depression, or canal) which is suitable for receiving the mouthpiece (200). For the avoidance of doubt, it is not the complete mouthpiece (200) as such which is accommodated in the groove (103), but only a portion thereof, e.g. the proximal segment or first segment (200a). The groove (103) typically extends from the air outlet opening (102) to the front of the base unit (100) and preferably has a horizontal orientation.

The base unit (100) may further exhibit one or more indentation(s) (106) whose position may be at or near the groove (103), and which are shaped to receive one or more protrusion(s) (204) of the mouthpiece (200). In this context, an indentation is a depression (or recess, or pit, or cavity, or void, or notch) whose "negative" shape is complementary to the "positive" shape of the protrusion (or projection, or nose, or bulge). Together, such indentations and protrusions act as positioning members or positioning indicators. The indentation, as well as the protrusion, may be asymmetrical such as to ensure that the component having the protrusion can only be inserted into the component having the indentation in one particular manner. In this way, the positioning members ensure that the device is assembled in such a way that the position and orientation of the components relative to each other are correct.

The base unit (100) may comprise one or more further indentation(s) (107), for example to receive one or more protrusion(s) (305) of the aerosol head (300) and/or of the mouthpiece (200). Such indentations may also function as positioning members to ensure the correct assembly of the device. The indentations as well as their complementary protrusions may optionally be asymmetrical.

Moreover, the base unit (100) may exhibit one or more electrical connector(s) (108) for electrically connecting it with complementary connectors of the aerosol head (300) in the assembled state. This is particularly important in case the aerosol head (300) comprises an ultrasonic or piezoelectric aerosol generator (301), such as a vibrating mesh-type aerosol generator (301).

The electricity powering the inhalation device may be supplied, for example, from an internal battery housed within the base unit (100) or from an external energy source connected to the base unit (100) via a cable. If the inhalation device is used as a mobile, stand-alone device, with the inspiratory air flow being provided by the user, an internal battery is preferred. Optionally, said internal battery is rechargeable. The recharge may be performed, for example, via an electrical connector (109), such as a USB-port, optionally during data transfer between the inhalation device and an external computer, as will be described further below. In a further embodiment, the device further comprises a battery indicator (113) for indicating the status of the battery, for example a control light, such as an LED. The status of the battery may, for example, be displayed by a green light ("on" for sufficient battery power, "off" for insufficient battery power) or by lights of different wavelengths (green for sufficient battery power, red for insufficient battery power, yellow indicating that battery should be replaced or recharged).

Optionally, the battery indicator (113) as well as other visual indicators of the inhalation device according to the invention are LEDs and housed within the base unit (100) in a "sunk-in" manner, such as not to protrude from the outer casing of the base unit (100). For example, the outer casing of the base unit (100) may cover the LEDs completely and may be prepared so as to be transparent, opaque or translucent at positions where an LED is placed beneath the casing.

If the inhalation device is designed as a handset for an inhalation system comprising further hardware components such as an external control unit capable of providing a controlled air flow, the energy supply to the base unit (100) may be received from the external control unit, for example via an electrical wire, or cable, attached to the electrical connector (109). Optionally, said electrical wire or cable, may be housed in a multi-luminal tube with at least two lumina; a first lumen for an air flow and a second lumen for holding an electrical wire. Such a multi-luminal tube may be used advantageously to supply, via one and the same tube, electrical energy as well as controlled air flow from the external control unit.

As mentioned, the base unit (100) exhibits one or more member(s) of a key lock (104), such as one or more male or female key lock members. The member(s) are complementary to the key lock member(s) (303) of the aerosol head (300). As used herein, a key lock is a releasable mechanical connection formed by two specific complementary members. Typically, the members are somewhat flexible, and one of the members (often referred to as "male") is inserted, clicked or hooked into, and/or caught by, the other member (often referred to as "female"). Release is usually very easy and achieved e.g. by slightly pressing the key lock, or one of the key lock members, such as in the case of a snap-fit connection.

Moreover, a key lock can be further customised in that—based on the same general connecting male-female-principle—particular shapes can be used for the key lock members which are only compatible with specifically complementary members. For example, there could be key locks of different width. In this manner, it can be prevented that components are assembled which belong to different devices or device versions. For example, an aerosol head (300) with an aerosol generator (301) which is specifically adapted for the delivery of a particular drug formulation (for example, by incorporating a vibrating mesh with a specific pore size) cannot be connected with a base unit (100) which is customised for the delivery of a different medicine (which may, for example, require a specific, preset flow rate), if the respective device versions exhibit key locks with different shapes. Thus the key locks may contribute not only to user convenience in terms of easy of device assembly and disassembly, but also to drug safety and the avoidance of medication errors.

Optionally, the approach of choosing key locks of different particular shapes for different device versions may be complemented by the use of different colours and/or patterns. For example, a coloured stripe may be printed horizontally around the base unit (100) in such a way that said stripe is only complete, or not interrupted, (i.e. running 360° all around the inhalation device) when the appropriate, complementary aerosol head (300) is attached to the base unit (100) and key lock members are engaged. Thus, different customised versions of the inhalation device, e.g. one having a thick red stripe, the other having a thin, green stripe, would also be easily distinguishable in a visual manner.

Optionally, the base unit (100) has two key lock members located at the two opposing left and right lateral vertical sides, or faces, of the base unit. As used herein, lateral, or laterally, means away from the middle, centre, or centre axis of the respective device or device component. Left and right should be understood from the perspective of the user holding the device appropriately under operational conditions. Positioning the key lock members on the opposing lateral vertical sides means that the device can be easily and conveniently disassembled by exerting gentle pressure on the key locks, holding the device between the thumb and e.g. the forefinger or the middle finger.

Optionally, the two key lock members (104) located at two opposing sides, or faces, of the base unit (100) are of identical shape, for example female key lock members of the same width on both left and right side. This allows for easier production of the base unit (100). However, they may also have different shapes, for example on one side a male, on the other a female member or a different width on each side, in order to prevent the attachment of the aerosol head (300) in a wrong orientation. Typically, the correct orientation of the aerosol head (300) is also assured by positioning members, such as e.g. an indentation (107) and a protrusion (305), as described above.

In one embodiment, the base unit (100) further comprises a means, such as a power switch (111), or button, to turn the inhalation device on or off; in particular where the device is designed as a mobile, stand-alone inhalation device where the user generates the inspiratory flow. In this case, the device may also comprise an on/off indicator (112), such as a control light, to show the on/off status of the base unit (100). The control light may be incorporated in the power switch (111), or button, or positioned in close vicinity of the button or switch.

When the inhalation device according to the invention is designed as a mobile, stand-alone device with the inspiratory flow being generated by the user, the base unit (100) further comprises an internal control unit which is capable of controlling or limiting the inspiratory air flow with regard to flow rate and inhalation volume, monitoring the patient's breathing pattern and providing a feedback, optionally visually, to the patient during inhalation.

Moreover, the control unit includes a storage means to store data such as target values or target ranges for inhalation parameters, records of a patient's breathing pattern during each inhalation treatment, which may be used for later analysis, such as compliance monitoring and/or therapy adjustments. All stored data can further be transferred to an external data handling device, for example a computer or a mobile phone, either wireless, e.g. via a Bluetooth connection, or via a cable connection with the electrical connector (109).

Optionally, the inhalation device is equipped with an electrical connector (109) in the form of a USB-port to allow attachment of a USB-cable which may serve as a data transfer means and/or as a recharge means for the above mentioned internal battery of the device.

As mentioned, the inhalation device may be equipped with a Bluetooth connectivity. In this case, the device may also comprise a connectivity indicator (114), such as a control light, for example an LED, to indicate the active/inactive status of the Bluetooth component. Such Bluetooth connections may be used to transfer data from the inhalation device of the patient to the computer of a caregiver, e.g. medicinal staff or doctor.

In a preferred embodiment, the device further comprises a flow restrictor (116), e.g. as described in EP 2 283 887 B1 and incorporated herein by reference, to restrict, control and/or regulate the inspiratory air flow of the patient, or to assist the patient to adopt a useful inspiratory flow rate. The flow restrictor (116) is designed to enable the patient or user to achieve a preset specific target value, for example 15 L/min, or target range, such as from 12 to 18 L/min. These flow rates are rather low compared to the inspiratory flow rates many patients use intuitively, especially when accustomed to pressurised metered dose inhalers and/or dry powder inhalers. Relatively low flow rates may however increase the fraction of inhaled drug which is deposited in the deeper, peripheral airways of the lungs, at the same time reducing oropharyngeal side effects. Thus they are considered beneficial in certain therapeutic settings.

The base unit (100) may further comprise a valve (118), such as a ball valve, which may be positioned within the air channel (110) of the base unit (100). Optionally, the valve (118) is electrically operated and capable of opening and closing the air channel (110). For example, the valve (118) may be adapted to close the air channel (110) after a preset inhalation time. If the air flow rate is controlled, the preset inhalation time would correspond to a specific inhalation volume.

Optionally, the device may be used for performing individual, patient-specific inhalation therapy using a preset inhalation time and/or inhalation volume which takes patient-specific parameters into account. For example, at the start of inhalation therapy, the patient may be subjected to an examination in order to assess the patient's forced expiratory volume in one second (FEV1) or inspiratory capacity (IC), which may then be used to calculate optimal treatment parameters for the respective patient. In this context, the method described in EP 2 067 497 A1 may be used.

Once the inhalation volume is selected, the respective inhalation time may be calculated in accordance with the preset target flow rate, such as 15 L/min. Thus, an inhalation volume of 1 L would correspond to a preset inhalation time of 4 seconds, after which the valve (118) shuts the air channel (110) off. The preselected inhalation time (or the actually remaining inhalation time) may be indicated to the patient by an inhalation time indicator (115), such as a light, which may be positioned close to the rear and/or at the top of the base unit (100). Optionally, a plurality of inhalation time indicators (115), such as LEDs, may be used whose number may correspond to a certain duration, for example one LED for every second of inhalation time. Alternatively, a particular indicator from a plurality of indicators may be used to indicate a specific preselected inhalation time. For example, a preset inhalation time of 6 seconds may be indicated by indicator number 6 being on.

In a further embodiment, the inhalation device may further comprise a feedback system to indicate to the user whether (or to what extent) an inhalation manoeuvre is being performed in such a way that a target parameter, such as a particular inspiratory flow rate, is complied with. The feedback system may be designed and configured as described in European Patent application 11195773.4, which is incorporated herein by reference. This feedback system will guide the user to perform inhalation maneuvers in an optimised manner with respect to predetermined values and/or ranges for inhalation parameters such as inspiratory flow rate, pressure, inspiration time, and/or inhaled volume. At least one of said inhalation parameters is selected from inspiratory flow rate and inhaled volume. Optionally, the feedback provided to the patient is acoustic, visual and/or tactile. One or more feedback signals may be provided for different inhalation parameters. The feedback system facilitates correction or adaptation of the inhalation manoeuvre by the user by indicating to the user means of feedback signal(s) whether the actual value of the inhalation parameter matches the predetermined target value or range. This may help to ensure the deposition of the inhaled aerosol in the target regions of the respiratory system.

The feedback system may include one or more sensor(s) (119) for sensing air pressure or air flow rate capable of generating a sensor signal in response to an actual value of flow rate and/or inhaled volume during the inhalation manoeuvre, an electronic memory capable of storing one or more target values and/or target ranges for flow rate and/or inhaled volume, one or more feedback indicator(s) (117) capable of emitting an output signal, and a controller capable of receiving the sensor signal(s) generated by the one or more sensor(s) (119), reading the electronic memory, and controlling the one or more feedback indicator(s) (117). The feedback system is configured to indicate to a user during an inhalation manoeuvre by means of the output signal(s) whether the actual value of the flow rate and/or inhaled volume is within a target range.

The one or more sensor(s) (119), for example pressure sensor(s) and/or flow sensor(s), sense the actual value of an inhalation parameter during inhalation and generate a signal corresponding to this value. For example, one or more flow sensor(s) may provide direct information on the flow rate which, by means of the internal clock included in the control unit, can be transferred into an indirect value for the inhaled volume. Flow rate values may further be obtained indirectly from pressure values provided by one or more pressure sensors, using calibration curves. The sensor signal(s) are sent to the controller where they will be compared to one or more predetermined target values and/or target ranges stored in the electronic memory. The one or more sensor(s) (119) are positioned within or in communication with an air channel (110, 207) of the inhalation device, whether within the base unit (100) or the mouthpiece (200). Accommodating the sensor(s) (119) within the base unit (100) offers the advantage of better protection and makes it easier to provide it/them with electrical connections.

The controller of the feedback system operates, or controls, the one or more feedback indicator(s) (117) in response to the signal(s) received by the one or more sensor(s) (119). The controller and its electronic memory are integral parts of the internal control unit housed within the base unit (100) of the mobile, stand-alone inhalation device according to the invention. Same applies to the internal clock which is required to measure inspiration time and/or to calculate indirect parameters, such as the inhaled volume from the flow rate.

The one or more feedback indicators (117) may, for example, comprise light sources, such as light-emitting diodes. For example, a light could be switched on when the patient's inhalation flow rate is within the preset target range of e.g. 12-18 L/min. Preferably, the feedback signal(s) provide a gradual feedback, for example, indicating i) whether the patient inhales at a flow rate falling within a preset operational range of the device, such as from 1-30 L/min; ii) whether the patient inhales at a flow rate falling within a preset optimal target range such as 12-18 L/min and/or iii) whether the patient inhales at a flow rate very close to a preset target value such as 15 L/min. Optionally, this gradual feedback is achieved visually by, for example, a green light of different intensity, with the light intensity reaching its highest value when the patient inhales at the most preferred flow rate target value. Such a gradual feedback enables the patient immediately, during each single inhalation, to adapt and correct his inspirational flow rate whenever necessary.

The mouthpiece (200) receives the nascent aerosol from the aerosol generator (301). In the mouthpiece (200), the aerosol is mixed or diluted with air while being carried downstream, and from the downstream end of the mouthpiece (200) the aerosol is eventually emitted via the aerosol outlet opening (203) and delivered to the mouth of the user. In the context of the invention, the mouthpiece (200) is understood as having a first segment (200a) which is insertable into the groove of the base unit (100) and a second segment (200b), which is downstream of the first segment (200a) and which extends from the base unit (100). For the avoidance of doubt, it is not necessary that the first (200a) and the second (200b) segments are separate parts. The first segment (200a) and the second segment (200b) may be made from the same or different materials. Optionally, they are made from an opaque or translucent material, such as opaque or translucent polypropylene.

The air channel (207) of the mouthpiece (200), which forms the downstream segment of the air channel of the inhalation device, extends from the air inlet opening (201) at the upstream end to the aerosol outlet opening (203) at the downstream end of the mouthpiece (200). The cross section of the air channel (207) may have an elliptical or circular shape. Advantageously, the shape and dimensions of the air inlet opening (201) match those of the air outlet opening (102) of the base unit (100) in order to allow an airtight connection. For this purpose, the air inlet opening (201) may be connectable with, or insertable into the air outlet opening (102), optionally via a sealing member (105), for example in form of a gasket, a sealing lip, gaiter, or any other type of seal, which serves to provide an airtight connection. The orientation of the air inlet opening (201) may be approximately vertical ($\pm 10°$) and thus about perpendicular to the direction of air flow. Optionally, the air inlet opening (201) may be covered with a mesh or filter, which should preferably exhibit a low flow resistance.

The mouthpiece (200) further comprises a lateral opening (202) for receiving the aerosol generator (301). The lateral opening (202) is preferably positioned at or near the upper side of the first segment (200a) of the mouthpiece (200). The shape of the lateral opening (202) may be circular. It may further comprise a sealing member (205), for example in form of a gasket, a sealing lip, gaiter, or any other type of seal, which serves to provide an airtight contact with the aerosol head (300), or with the aerosol generator (301), respectively. The orientation of the lateral opening (202) may be approximately horizontal and perpendicular to the plane of the air inlet opening (201).

As mentioned, the nascent aerosol from the aerosol generator (301) is introduced into the air channel (207) where it is diluted, or mixed, with the air flowing through the air channel (207). Thus, the air channel (207), or the respective region of the air channel (207) of the mouthpiece (200), may also be referred to as a mixing channel. The shape and dimensions of the air channel (207), or mixing channel, may be selected as described in European Patent application 12158852.9, which is incorporated herein by reference. Following the guidance provided in this document results in a homogenous distribution of droplets in the nascent aerosol and a reduced loss of aerosol droplets in the inhalation device due to coalescence and/or deposition within the device by impaction and/or sedimentation.

However, since deposition losses can never be completely avoided, such depositions should be removed by cleaning regularly, e.g. by thoroughly rinsing all affected parts with tap water. Since the nascent aerosol enters directly into the first segment (200a) of the mouthpiece (200) through the lateral opening (202) and immediately gets carried downstream towards the aerosol outlet opening (203) it does not come in contact with the base unit (100). Hence, the base unit (100) stays free of undesirable aerosol depositions. This advantageously avoids the need to rinse the base unit (100) which houses the water-sensitive electronics.

In particular, the air channel (207), or mixing channel, may be shaped to include a step (206) on its inner circumferential surface. This step (206), which may be defined as an abrupt change in the cross sectional area at a longitudinal locus or within a short longitudinal section, creates a discontinuity in the direction of the air flow. Preferably, the cross sectional area decreases abruptly at the injection zone where the aerosol droplets are introduced from the aerosol generator (301) into the air channel (207). The step (206) is positioned adjacent to the downstream end (306b) of the aerosol generator (301) which may protrude into the air channel (207). Optionally, the step (206) may also be formed by said downstream end (306b) of the aerosol generator (301) itself. The abrupt decrease of the cross sectional area within the injection zone will accelerate the air flow in the narrowed, or constricted, region and cause turbulences. While the turbulences ensure sufficient mixing of the nascent aerosol droplets with air, the accelerated air flow reduces the density of the nascent aerosol by increasing the distance between the individual droplets in the direction of the air flow and thus avoids undesirable coalescence. The magnitude of the turbulences and the air flow acceleration correlates with the degree to which the step (206) extends, or protrudes, into the air channel (207), or mixing channel; a 50% decrease, for example, provides sufficient mixing while at the same time avoiding aerosol particle impaction and/or coalescence. Owing to this type of mixing channel, more spacious mixing chambers can be avoided, thereby reducing the dimensions of the inhalation device. Specifically, the height of the device can now be chosen in way as to not exceed, or only marginally exceed its width, when looking at the front side. It should be noted that the step (206) in the inner circumferential surface is independent of the air channel's (207) outer circumferential surface; i.e. the outer walls of the air channel (207) may not always reflect the step (206).

Downstream of the narrowed, or constricted, region within the injection zone, the air channel (207) preferably widens like a truncated cone in order to decelerate the air flow to a flow rate at the aerosol outlet opening (203) which is suitable for inhalation, and which helps to avoid or at least to reduce deposition of the aerosol droplets on the inner wall of the air channel (207). Such deposition may be further reduced by suitable anti-static coatings on the inner wall. Again, the increasing cross sectional inner surfaces of the truncated cone shaped air channel (207) may not reflect in the cross sectional outer surfaces.

The mouthpiece (200) further has an aerosol outlet opening (203), whose shape may be elliptical or circular, positioned in the second segment (200b) at the downstream end of the air channel (207). The orientation of the aerosol outlet opening (203) may be approximately vertical in normal mode of use. The dimensions of the downstream end of the second segment (200b) and of the aerosol outlet opening (203) are chosen in such a way that the patient can easily place this part of the mouthpiece (200) in his mouth while ensuring that the mouth is opened widely enough for optimal aerosol administration. Optionally, mouthpieces with a slightly smaller downstream end of the second segment (200b) may be provided for toddlers and children.

As mentioned before, the aerosol head (300) comprises an aerosol generator (301), a reservoir for a liquid (302) and one or more key lock member(s) (303) which may be male or female, and which are complementary to the key lock member(s) (104) of the base unit (100), so that the base unit (100) and the aerosol head (300) are easily connectable via a simple key lock, or snap-fit, connection. The aerosol head (300) may be shaped in such a way that, in an assembled state of the inhalation device, it covers any voids created by the groove (103) and/or indentations (106, 107) which are not already covered by the inserted first segment (200a) of the mouthpiece (200).

The aerosol head (300) comprises, at its upstream end, a reservoir (302) for holding a liquid to be nebulised, which is in fluid contact with the upper end of the aerosol generator (301). The reservoir (302) is optionally shaped as a funnel, or truncated cone, or a tapered cylinder, with the narrower end transitioning into the upstream end (306a) of the aerosol generator (301), such as to ensure easy, gravity-driven liquid flow from the reservoir (302) into the aerosol generator (301). If the dimensions of the inhalation device are chosen such that the height does not exceed, or only marginally exceeds, the width (when looked at from the front), tilting or tipping of the inhalation device during the filling of the reservoir (302) are prevented. Spillage of the liquid drug formulation during use, or its contamination, is preferably prevented by a lid (304) which closes the upper end of the reservoir (302). Preferably, the lid (304) is a removable cap, such as a screw cap, a hinged flip-top lid or a removable snap-on lid with sealing lips.

The aerosol head (300) further comprises an aerosol generator (301) which may be positioned centrally in the aerosol head (300) in such a way that when engaging the male or female key lock member(s) (303) of the aerosol head (300) with the complementary key lock member(s) (104) of the base unit (100), the aerosol generator (301) is at least partially inserted, with its downstream end (306b), into the lateral opening (202) of the first segment (200a) of the mouthpiece (200). Preferably, the aerosol generator (301) is a vibrating mesh-type aerosolizer comprising a mesh (309), or microperforated membrane, capable of vibration wherein a nebulised aerosol is generated.

An example of a particularly useful aerosol generator is described in WO 2008/058941 A1, which is incorporated herein by reference. This device is an ultrasonic liquid atomiser comprising a piezoelectric transducer body (306), for example made of stainless steel, titanium or aluminium, which encloses a cavity (307) for containing the liquid to be atomised. The transducer body (306) and the cavity (307) are symmetrical along the axis X. The cavity (307) is arranged to be in fluid contact with the reservoir (302) so as to receive liquid to be nebulised from the reservoir (302).

The piezoelectric transducer body (306) further comprises a piezoelectric member (308), preferably an annular single or multilayer ceramic, which vibrates the piezoelectric transducer body (306) in a longitudinal mode, at a frequency preferably in the 50 to 200 kHz range. As a result, micronic longitudinal displacements, or deformations, occur in a direction parallel to the transducer body's (306) symmetry axis X. The piezoelectric transducer body (306) exhibits a region close to the piezoelectric member (308) with a relatively large wall thickness, which serves as a stress concentration zone (306c), and a region downstream thereof with a relatively low wall thickness which serves as a deformation amplification zone (306d). In this configuration, the vibrations or deformations of the piezoelectric transducer body (306) caused by the piezoelectric member (308) are amplified. Preferably, the piezoelectric member (308) is located at the level of, or adjacent to, the stress concentration zone (306c). The internal diameter of the transducer body (306) at the deformation amplification zone (306d) may be the same as at the stress concentration zone (306c), so that the differences in wall thickness correspond to different external diameters. Alternatively, the external diameter of the transducer body (306) may be constant, while the inner diameters differ at the position of the two zones.

A mesh (309), or micro-perforated membrane, may be positioned at the downstream end (306b) of the transducer body (306). The micro-perforations may be formed by electroforming or by laser drilling, with openings normally being in the range from about 1 μm to about 10 μm. Without vibration of the mesh (309), the balance of pressures, the shape of the holes and the nature of the material used for the mesh (309) are such that the liquid does not seep out through the mesh (309). However, vibration of the mesh (309) leads to the formation and emission (or extrusion) of aerosol droplets through the mesh (309). The mesh (309) may be made of plastic, silicon, ceramic or more preferably metal, and may be affixed to the downstream end (306b) of the aerosol generator (301) by various means, such as gluing, brazing, crimping or laser welding. Optionally, the mesh (309) at least partially forms a dome in its central region, which causes the jet of nascent aerosol droplets to diverge and hence reduces the risk of droplet coalescence.

The aerosol head (300) may receive electrical power and signals for operating and controlling the aerosol generator (301) from the base unit (100) via electrical connectors which connect with the electrical connectors (108) of the base unit in the assembled state.

As described earlier, the aerosol head (300) further comprises male or female key lock member(s) (303) which are complementary to the key lock member(s) (104) of the base unit (100). In one embodiment, the aerosol head (300) has two key lock members (303) located at the two opposing left and right lateral vertical sides, or faces, of the aerosol head (300). This offers the advantage that base unit (100) and aerosol head (300) are easily detachable from one another by gently pressing both sides with e.g. thumb and index finger. With respect to the shapes, dimensions and customisation options of the key lock member(s) (303), reference is made to the respective discussion in the context of the key lock member(s) (104) of the base unit (100).

As explained above, the inhalation device of the invention brings about substantial advantages. Due to the small number of major components, it is easy for a user to assemble the device and prepare it for an inhalation treatment session. This is convenient and time-saving, but also adds to the coherence of patients to their prescribed therapy. It reduces the risk that a patient who might find it generally difficult to assemble a device, for example an elderly or sick person, becomes discouraged with the device or even discontinues the prescribed inhalation therapy. Quick and easy disassembly is just as important as the user, or patient, will find it easier to clean and disinfect the device regularly, as needed. It is noted that patients who do not regularly clean and/or disinfect their inhalation device are at an increased risk of developing an infection or superinfection of the respiratory system, or a part thereof.

Moreover, the inhalation device of the invention, in particular with its preferred embodiments, ensures the correct assembly of the device. For example, the special configuration of the main components ensure that when the key locks are engaged, the aerosolizer is automatically in the correct position, and all important members of the device have the correct orientation. Thus, the risk of major user errors potentially leading to device malfunction or even lack of delivery of the aerosolised medicament to the patient is greatly reduced.

Another advantage of the invention is that it provides an excellent platform for efficient and cost-effective customisation. On the one hand, customisation is a feature enhancing drug safety. For example, a particular aerosol head adapted for the inhalation therapy with a first medicament (e.g. with respect to the dimensions of the reservoir or of the opening of its vibratable mesh) may be customised by means of a special shape or geometry of its key lock member(s) so that it can only be assembled with the correct base unit which is also adapted (and e.g. programmed) for the delivery of this medicament, and cannot be combined with a different base unit adapted for the delivery of another medicament. This is an important safety issue since it is of course possible that the same patient, or another member of the same household, has also a prescription for another inhalable medicament. On the other hand, customisation needs to be economically feasible, which is the case with the present invention as the same device may be manufactured in several customised versions which share many basic device components.

Moreover, the low number of main components that must be assembled for use requires that only few airtight connections must be established during assembly, thus increasing the overall airtightness of the assembled device, which in turn enhances it reproducible functionality and delays the occurrence of air leaks through wear over time.

Certain embodiments of the invention are now explained with reference to FIGS. 1 to 7.

FIG. 1 shows an exploded view of a particular inhalation device according to the invention, comprising a base unit (100), a mouthpiece (200) and an aerosol head (300). The base unit (100) is roughly shaped like a flat, rounded cuboid, exhibiting a groove (103) for receiving the mouthpiece (200). An air outlet opening (102) is positioned in a central region of the base unit (100). From this perspective, no air inlet opening(s) (101) can be seen. A female key lock member (104) is seen on the left hand side (seen from the perspective of the user during inhalation), whereas another key lock member on the right hand side is partially hidden. The mouthpiece (200), which is partially insertable into the groove (103) of the base unit (100), exhibits an air inlet opening (201) at its upstream end and an elliptical aerosol outlet opening (203) at its downstream end. In an upper position of the mouthpiece (200), a lateral opening (202) is present. The aerosol head (300) has two male key lock members (303), one on each of the left and right hand side of the aerosol head (300). From the aerosol generator (301), only the bottom part is visible. The reservoir (302) is located in the upper region of the aerosol head (300). A lid (304) is screwable onto the aerosol head (300) such as to cover the reservoir (302). Correct assembly of the inhalation device is easily and conveniently achievable by inserting the mouthpiece (200) into the groove (103), which will cause the aerosol generator (301) to be partially inserted into the lateral opening (202) of the mouthpiece (200), and gently pressing the aerosol head (300) onto the main body (100) in such a way that the male key lock members (303) of the aerosol head (300) engage with the female key lock members of the main body (100). After filling a liquid to be aerosolised into the reservoir (302), the reservoir (302) may be closed with the screw-on lid (304). For disassembly, the male key lock members (303) are gently squeezed for disengagement, and the aerosol head (300) may be lifted off from the main body (100).

Figure 2:
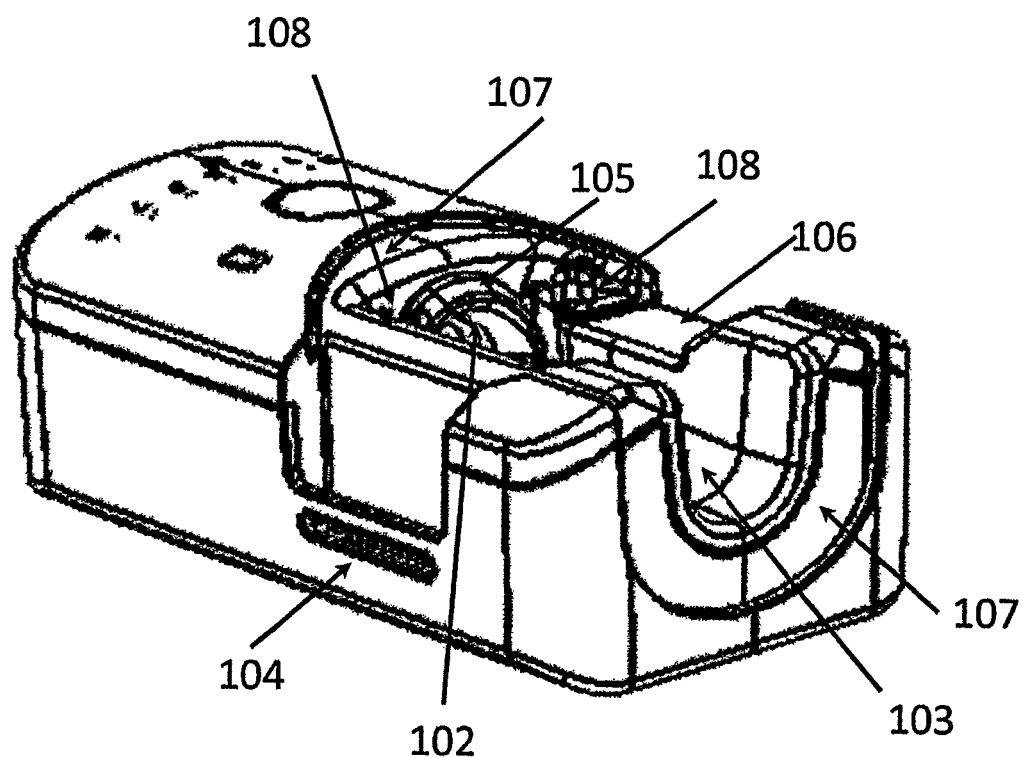
FIG. 2 shows an enlarged view of the base unit of FIG. 1.

FIG. 2 shows an expanded view of the base unit (100) of FIG. 1. It illustrates a ring-shaped sealing member (105) of the air outlet opening (102) which ensures an airtight connection with the mouthpiece. Moreover, indentations (106, 107) are shown which are designed as positioning members in that they are shaped to receive corresponding protrusions of the mouthpiece and of the aerosol head. The base unit (100)

further exhibits two electrical connectors (108) for connecting the aerosol head to the base unit (100).

Figure 3:
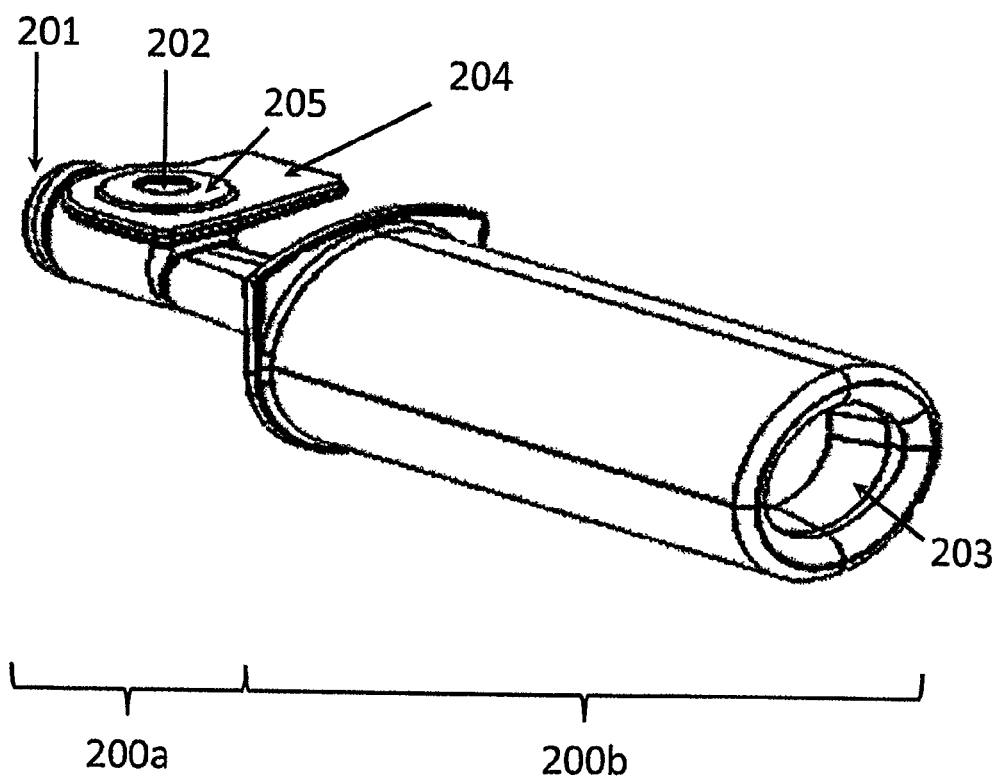
FIG. 3 shows an enlarged view of the mouthpiece of FIG. 1.

FIG. 3 shows an expanded view of the mouthpiece (200) of FIG. 1, having a first segment (200a) and a second segment (200b) downstream of the first segment. The first segment (200a) is shaped such as to be insertable into the groove of the base unit, whereas the second segment (200b) is not insertable. The mouthpiece (200) further exhibits a positioning member shaped as a protrusion (204), which is complementary to an indentation of the base unit. The circular lateral opening (202) is equipped with a ring-shaped sealing member (205) to ensure a tight connection with the aerosol generator.

Figure 4:
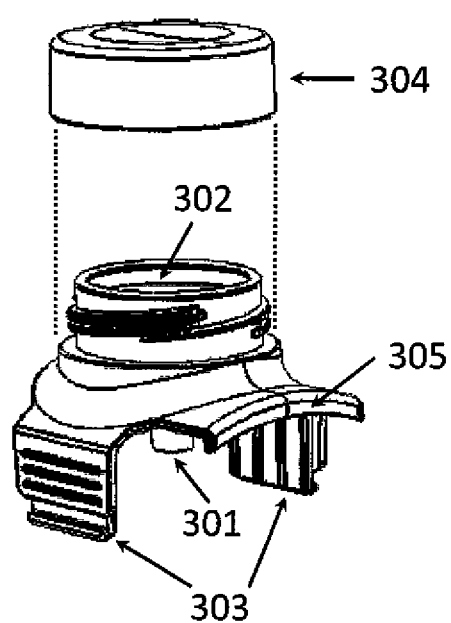
FIG. 4 shows an enlarged view of the aerosol head of FIG. 1.

FIG. 4 shows an expanded view of the aerosol head (300) of FIG. 1, exhibiting a positioning member in the form of a protrusion (305) which matches a corresponding indentation of the base unit.

Figure 5:
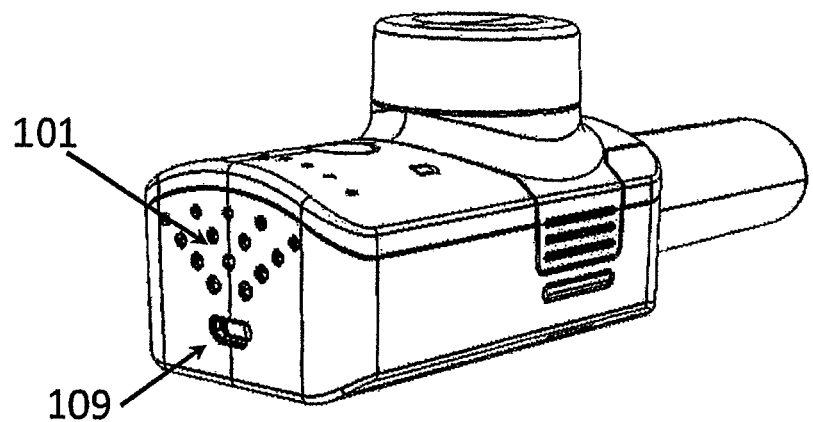
FIG. 5 shows a three-dimensional rear view of the inhalation device of FIG. 1 in assembled form.

FIG. 5 shows a three-dimensional rear view of the inhalation device of FIG. 1 in assembled form. In the rear of the device, several air inlet openings (101) and an electrical connector (109), here in the form of a USB port, can be seen.

Figure 6:
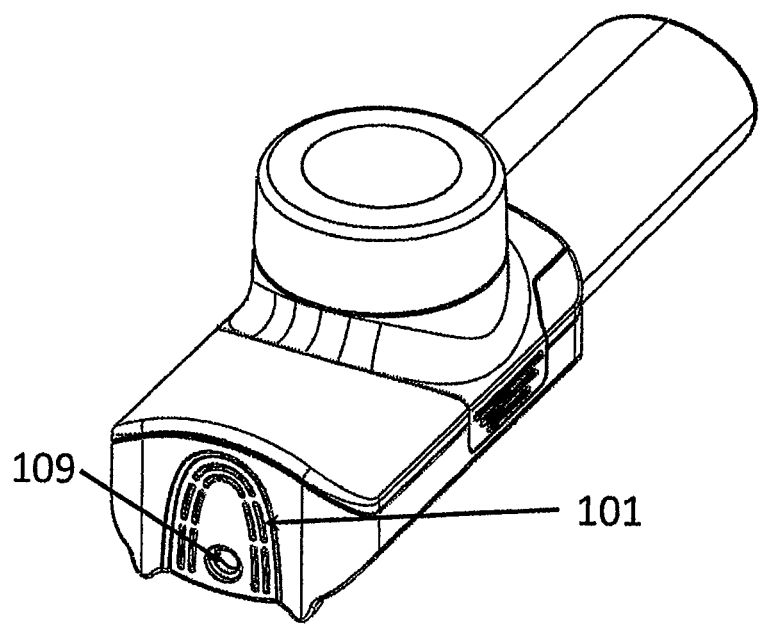
FIG. 6 shows a three-dimensional rear view of an alternative embodiment of the inhalation device in assembled form.

FIG. 6 shows a three-dimensional rear view of an alternative embodiment of the inhalation device, exhibiting multiple air inlet openings (101) and an electrical connector (109) for connecting the device with an external control unit or other hardware component via a multi-luminal tube.

Figure 7:
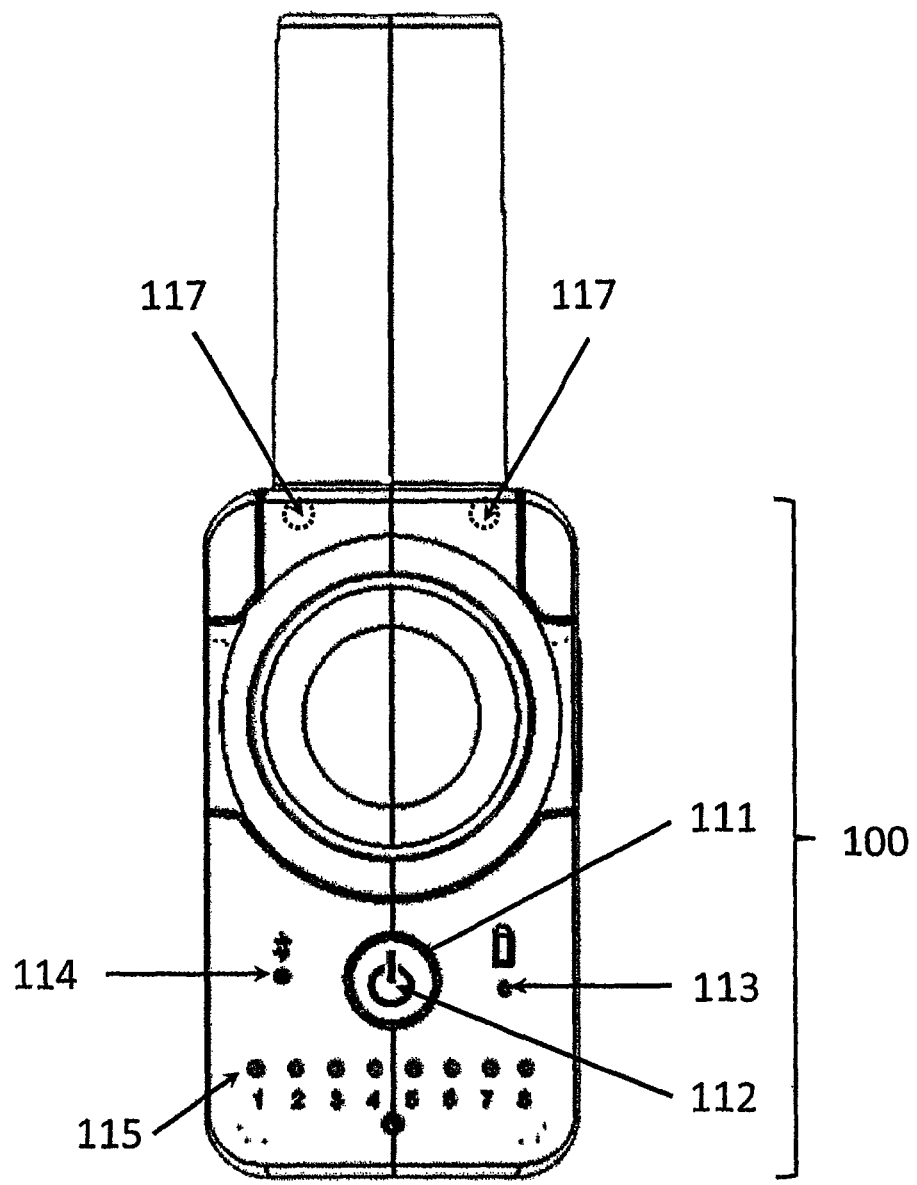
FIG. 7 shows a top view of the inhalation device of FIG. 1 in assembled form.

FIG. 7 gives a top view of the inhalation device of FIG. 1 in assembled form. It illustrates how a base unit (100) may be equipped to have a power switch (111) with an integrated on/off indicator (112) for manually switching the inhalation device on and off and verifying the status of the device; a battery indicator (113) for indicating the status of the battery; a connectivity indicator (114) for indicating the availability and/or status of a data connection e.g. to an external computer or mobile phone; eight inhalation time indicators (115) for indicating the preset inhalation time per breathing manoeuvre; two feedback indicators (117) in the form of LEDs incorporated in the frontal part of the base unit (100) to indicate to the user whether or to what extent an ongoing inhalation manoeuvre conforms to a target parameter such as a target inspiratory flow rate.

Figure 8:
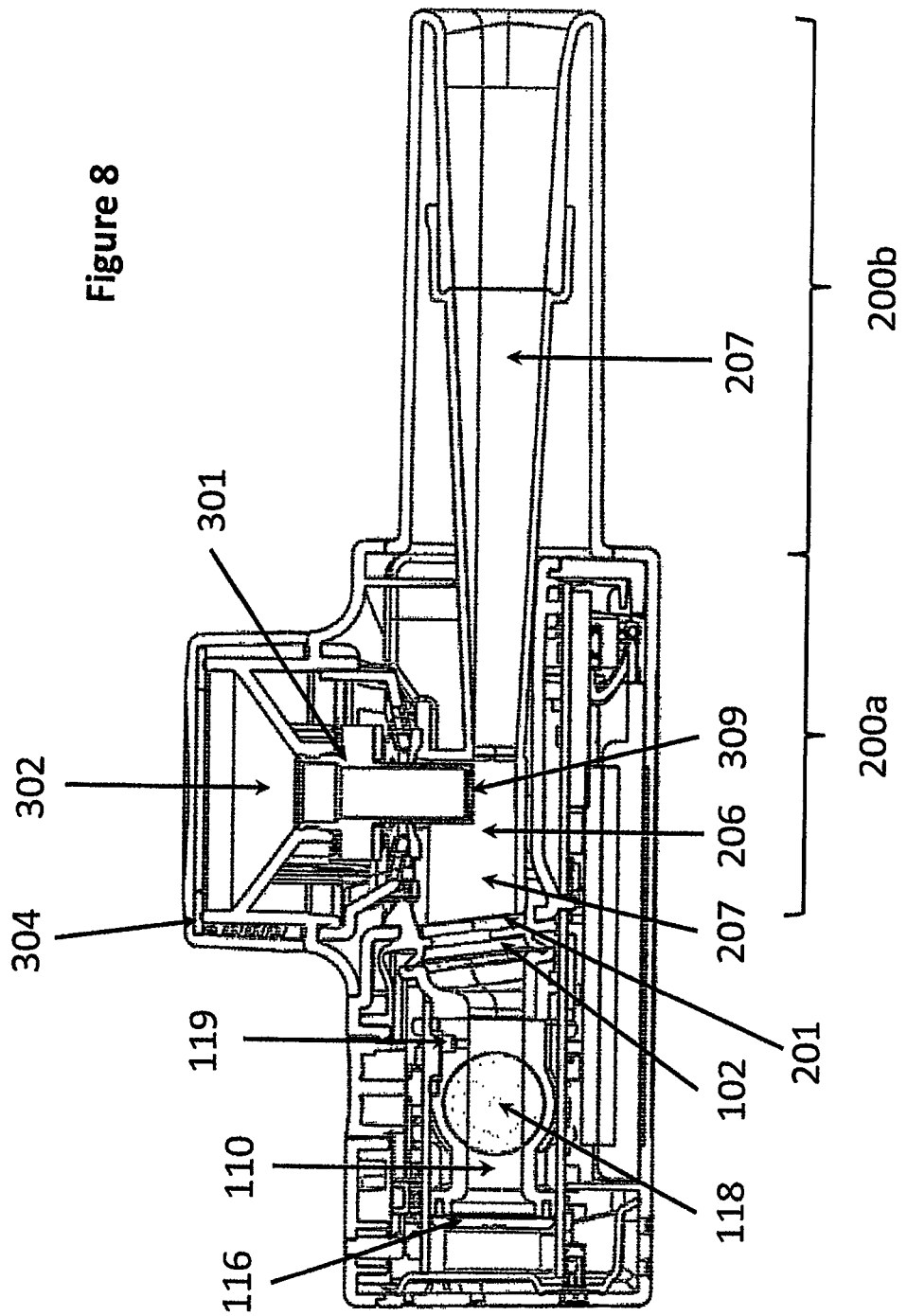
FIG. 8 shows a cross-section of a particular embodiment of the inhalation device in the assembled state.

FIG. 8 shows a longitudinal, vertical cross-section of a particular embodiment of the inhalation device in the assembled state. It illustrates how the first segment (200a) of the mouthpiece (200) is accommodated within the base unit (100), whereas the second segment (200b) extends from it such that it can be placed into the mouth of a user. The aerosol generator (301) is partially inserted into the air channel (207) of the mouthpiece (200) so that its downstream end (306b) reaches a position near the longitudinal centre axis (not shown) of the air channel (207) within the first segment (200a). Upstream of the inserted portion of the aerosol generator (301), the air channel (207) exhibits a much larger cross-sectional area than downstream. Here, the narrowing of the air channel (207) is abrupt in the form of a step (206). Towards the downstream end of the mouthpiece (200), the air channel (207) widens such as to form a tapered cylinder or truncated cone. The air inlet opening (201) of the mouthpiece (200) is connected to the air outlet opening (102) of the base unit (100). The Figure also shows a sensor (119), such as a pressure or flow sensor, which is positioned to be in communication with the air channel (110) of the base unit (100). A valve (118), in this case in the form of a ball valve, is positioned within the air channel (110) of the base unit (100) such as to be able to shut off any air flow within the air channel (110). Further upstream, a flow restrictor (116) is positioned to restrict the air flow, which is configured to prevent undesirably high flow rates and/or to make it easier for a user to breathe slowly. Also shown is the position and tapered shape of the reservoir (302) in the aerosol head (300), which is closed by a screw-on lid (304).

Figure 9:
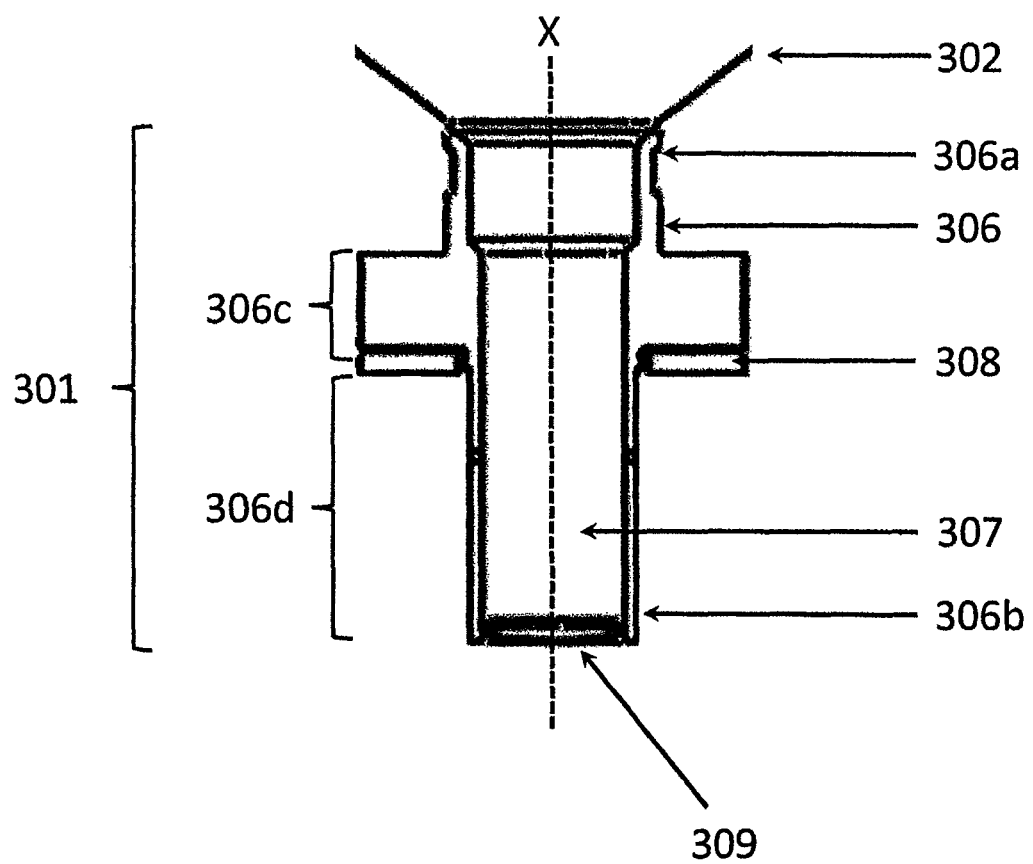
FIG. 9 shows a cross section of the aerosol generator of FIG. 8.

FIG. 9 shows a cross section of the aerosol generator (301) of FIG. 8, comprising a transducer body (306) having a stress concentration zone (306c) and a deformation amplification zone (306d), an upstream end (306a) and a downstream end (306b). The wall thickness of the stress concentration zone (306c) is considerably larger than that of the deformation amplification zone (306d), and while the internal diameter is substantially the same for both zones, their external diameters differ. A piezoelectric member (308) is located in the position where the two zones meet. The upstream end (306a) of the transducer body (306) is connected to the reservoir (302) for holding the liquid to be nebulised. Moreover, the longitudinal centre axis (X) is shown.

The invention claimed is:

1. An inhalation device comprising a base unit, a mouthpiece, and an aerosol head, wherein:
  (a) the base unit comprises:
    one or more air inlet opening(s)
    an air outlet opening,
    a groove for receiving the mouthpiece, and
    one or more key lock member(s);
  (b) the mouthpiece comprises:
    a first segment, comprising
      an air inlet opening connectible with the air outlet opening of the base unit, and
      a lateral opening for receiving an aerosol generator,
    the first segment being insertable into the groove of the base unit, and
    a second segment downstream of the first segment, comprising an aerosol outlet opening; and
  (c) the aerosol head comprises:
    an aerosol generator,
    a reservoir for a liquid,
    one or more key lock member(s) complementary to the key lock member(s) of the base unit; and
  wherein the base unit, the mouthpiece and the aerosol head are connectible with one another; and
  wherein the aerosol generator is positioned in the aerosol head in such a way that when engaging the member(s) of the key lock with the complementary member(s), the aerosol generator is at least partially inserted into the lateral opening of the first segment of the mouthpiece.

2. The inhalation device of claim 1, wherein the groove has a horizontal orientation and extends from the air outlet opening of the base unit to a front side of the base unit.

3. The inhalation device of claim 1, wherein the first segment of the mouthpiece comprises a protrusion, and wherein the base unit comprises an indentation for receiving the protrusion.

4. The inhalation device of claim 3, wherein the protrusion is asymmetric.

5. The inhalation device of claim 1, wherein the base unit and the aerosol head each comprise two key lock members, and wherein the key lock members are positioned to form a key lock on a left side and another key lock on a right side of the inhalation device.

6. The inhalation device of claim 5, wherein the key locks may be disengaged by squeezing the aerosol head at the position of the key lock members.

7. The inhalation device of claim 1, wherein the lateral opening of the mouthpiece for receiving the aerosol generator is positioned on a top side of the first segment of the mouthpiece, and wherein the aerosol head is positioned on a top side of the inhalation device.

8. The inhalation device of claim 1, wherein the aerosol generator comprises a mesh capable of vibration, and wherein a nebulised aerosol is generated by the vibration of the mesh.

9. The inhalation device of claim 8, wherein the aerosol generator has an upstream end positioned at a top of the aerosol generator and a downstream end positioned at a bottom of the aerosol generator, and wherein the mesh is located at or near the downstream end.

10. The inhalation device of claim 1, wherein the air outlet opening of the base unit and/or the lateral opening of the mouthpiece for receiving the aerosol generator exhibits a sealing member.

11. The inhalation device of claim 1, wherein the base unit and the aerosol head comprise electrical connectors positioned in such a way that when engaging the base unit's member(s) of the key lock with the aerosol head's complementary member(s) the electrical connectors of the base unit are brought in contact with the electrical connectors of the aerosol head.

12. The inhalation device of claim 1, wherein the base unit comprises
   (a) one or more sensor(s) for sensing air pressure or air flow rate within the base unit, and/or
   (b) a valve for opening or closing an air flow within the unit, and/or
   (c) an electronic control unit for controlling the aerosol generator and/or the valve.

13. The inhalation device of claim 1, wherein the device comprises a feedback system, said feedback system comprising:
   (a) one or more sensor(s) for sensing air pressure or air flow rate and capable of generating a sensor signal in response to an actual value of flow rate and/or inhaled volume during an inhalation manoeuvre;
   (b) an electronic memory capable of storing one or more target values and/or target ranges for flow rate and/or inhaled volume
   (c) one or more feedback indicator(s) capable of emitting an output signal; and
   (d) a controller capable of receiving the sensor signal(s) generated by the sensor(s), reading the electronic memory, and controlling the one or more feedback indicator(s);
   wherein the feedback system is configured to indicate to a user during the inhalation manoeuvre by means of the output signal(s) whether the actual value of the flow rate and/or inhaled volume is within a target range.

14. The inhalation device of claim 1, wherein the one or more air inlet opening(s) of the base unit are connected to a tube through which an air flow is received, and wherein the tube optionally exhibits a first lumen for an air flow and a second lumen holding an electrical wire.

15. The inhalation device of claim 1 for the use in inhalation therapy.

\* \* \* \* \*